United States Patent [19]

Gross et al.

[11] 4,029,632

[45] June 14, 1977

[54] PROSTHETIC DENTAL APPLIANCE

[75] Inventors: Albert Gross, Frankfurt am Main;
Roland Schaefer, Friedrichsdorf,
Taunus, both of Germany

[73] Assignee: Kulzer & Co., GmbH, Bad Homburg
vor der Hohe, Germany

[22] Filed: Feb. 3, 1975

[21] Appl. No.: 546,339

[30] Foreign Application Priority Data

Feb. 6, 1974 Germany .................... 2405578

[52] U.S. Cl. .................... 260/42.15; 32/15;
260/998.11

[51] Int. Cl.² .................... C08K 9/06

[58] Field of Search .............. 32/15; 106/35, 288 B;
260/42.15, 998.11, 47 EP; 423/325, 336, 337

[56] References Cited

UNITED STATES PATENTS

| | | | |
|---|---|---|---|
| 2,036,728 | 4/1936 | Simon | 32/15 |
| 2,477,268 | 7/1949 | Saffir | 260/998.11 |
| 3,066,112 | 11/1962 | Bowen | 260/37 EP |
| 3,709,866 | 1/1973 | Waller | 260/27 R |
| 3,769,336 | 10/1973 | Lee et al. | 260/486 R |
| 3,845,009 | 10/1974 | Gander | 106/35 |

FOREIGN PATENTS OR APPLICATIONS

| | | |
|---|---|---|
| 240,687 | 1/1959 | Austria |
| 1,146,617 | 4/1963 | Germany |
| 827,699 | 2/1960 | United Kingdom |

*Primary Examiner*—Theodore Morris
*Attorney, Agent, or Firm*—Flynn & Frishauf

[57] ABSTRACT

The present invention provides prosthetic dental appliances which contain at least one outer surface portion which includes an outer surface of the appliance which is adapted to be polished and which is highly abrasion resistant. Said shaped body portion is a hardened matrix material containing amorphous silicic acid filler particles of a maximum particle size of about 0.07 micrometer. Preferably, at least 30% of the body portion comprises the filler particles. The polymeric matrix is preferably a hardened organic resin. The invention also includes the hardenable material comprising a hardenable matrix having filler paticles dispersed therein which is used to produce the hardened prosthetic dental appliances.

30 Claims, 3 Drawing Figures

PROSTHETIC DENTAL APPLIANCE

The present invention relates to prosthetic dental appliances and, more particularly, to artificial teeth, bridges, crowns, jacket crowns, and the like, i.e., generally, to teeth and prosthetic or replacement elements for teeth.

Dental prosthetic appliances should have the structural strength of teeth and, additionally, present as natural an appearance as possible. The prosthetic appliances should therefore be capable of being polished, while still being pressure resistant, have at least some surface transparency, and desired hardness, and mechanical strength. In general, two important characteristics of dental prosthetic appliances (namely, the capability of being polished and resistance to abrasion) are opposed to each other since the higher the capability of accepting polish or smooth surface, the less resistance to abrasion. These mutually opposite characteristics are described, for example, in German disclosure document DT-OS2312258.

It is an object of the present invention to provide dental prosthetic appliances, such as artificial teeth, bridges, caps, crowns, jacket crowns, or the like which have high resistance to abrasion while being capable of being polished to a smooth sheen or gloss.

SUBJECT MATTER OF THE PRESENT INVENTION

The present invention provides prosthetic dental appliances, such as artificial teeth, crowns, caps, bridges, jacket crowns, and the like. At least one outer surface portion of such appliance which includes an outer surface which is to be highly polished and which is to be highly resistant to abrasion comprises a hardened polymeric matrix containing amorphous silicic acid filler particles of a maximum particle size of about 0.07 micrometer. Thus, the entire dental appliance need not be made up of said polishable and abrasion-resistant material containing said hardened polymeric matrix loaded with said filler particles. Instead, it may be particularly concentrated or located at the exterior surface of the tooth or other dental appliance.

The invention also provides a hardenable material containing the said amorphous silicic acid particles dispersed in a polymerizable matrix which may be hardened in a mold, e.g., a mold of a tooth or cap or bridge and in the case of a tooth being filled may be the cavity in the tooth, to form a hardened material which is abrasion resistant and which will take a high polish.

A BRIEF DESCRIPTION OF THE DRAWINGS

Figure 3:
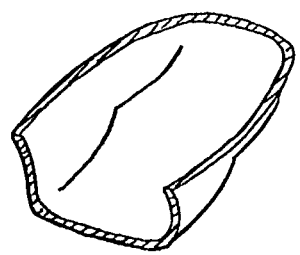

and FIG. 3 is a highly schematic, perspective view of a cap or jacket crown in accordance with the present invention.

Figure 1:
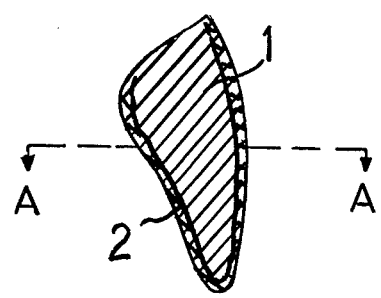
FIG. 1 is a longitudinal sectional view along the plane B—B of FIG. 2 through an artificial tooth.

The tooth of FIG. 1 includes a core 1 which is made of a binder material, and an outer jacket or sheath 2 which includes binder and filler. The jacket crown of FIG. 3 is entirely made of a material including both binder and a filler.

The filler comprises very fine particles of amorphous silicic acid, with a maximum particle size of 0.07 micrometer. Amorphous silicic acid is to be understood to be silicic acid which has been precipitated or generated by flame hydrolysis (fuming), and which may contain up to 20% (by weight) of aluminum oxide. Preferably, at least half of the filler particles are of a size range in order of from 0.03 to 0.05 micrometers.

The filler material comprising amorphous silicic acid may have finely dispersed glass added thereto in quantities up to about 25 percent (by weight) of the entire filler material. Borosilicate glass, barium oxide-containing glass or lanthanum oxide - containing glass for example may be used. Lithium aluminum silicate glass is preferred. The filler material is contained in a binder capable of being hardened, usually by being polymerized. Such a binder may, for example, be a polymerizable monomer, capable of being polymerized by a catalyst. The term "binder" as used herein refers to (i) the hardened binder material, preferably a polymerized resin, which forms a hardened matrix for the filler particles, and also to (ii) the polymerizable chemicals (usually monomers) which are polymerized to form the hardened matrix.

In order to match the color or shade or hue of the resulting dental appliance to the existing teeth, organic and/or inorganic pigments, or materials decreasing the light transmissivity may be added; i.e., materials (opacifiers) which render the resulting tooth or appliances more opaque.

Polymerizable monomeric binders which are particularly suitable for the present invention are, for example, mono-, di-, and higher esters of methacrylic acid, particularly Bis-GMA (defined below). Diluting monomers, such as methylmethacrylate, may be used. Other examples of monomer binders are:

2,2-bis-[p- (2-hydroxyethoxy)-phenyl]-propanedimethacrylate; and triethyleneglycoldimethacrylate.

A filling material for dental use has previously been proposed (see German disclosure document DT-OS2164668) which consists of a mixture of a liquid polymerizable organic binder, such as bis-[4-(2-hydroxy-3-methacryloyloxypropoxy)-phenyl]-dimethylmethane which is the reaction product of bisphenol A and glycidylmethacrylate, commonly abbreviated as Bis-GMA, in admixture with triethyleneglycoldimethacrylate, as a diluting monomer, and a solid inorganic filler. The filler in accordance with said disclosure consists of glass-like particles which have a diameter of between 0.7 and 30 micrometers. At least half of the filler components, by weight, are in the region of a size of less than 20 micrometers. To increase adhesion between the filler particles and the binder, it has been proposed to treat the filler particles with tri-(2-methoxyethoxy)-vinylsilane. This known filling material for teeth, when hardened, is capable of being polished without decrease in resistance to compression, transparency, hardness and tensile strength.

An abrasion-resistant material for dental prosthetic appliances has been proposed in German disclosure document DT-OS2312258. It is based on polymer mixtures containing dispersed fine inorganic filler material. The filler material are glass or ceramic particles having a minimum size of 0.8 to 8 micrometers and a maximum size in the region of between 3 and 20 micrometers.

The dental prosthetic appliances, in accordance with the present invention, have a content of filler material of from 30 to 80 percent (by weight), preferably, about 50 to 70 percent (by weight). The amorphous silicic acid is preferably silanated (treated with an organic silane), for example, trimethoxy-(3-methacryloyloxypropyl)silane. Contrary to expectation and entirely unexpectedly, the dental appliances of the present invention have the advantage of being highly abrasion resistant and of being suitable to be highly polished. These characteristics were in the past considered to be mutually opposed.

Catalysts, in whose presence polymerization will occur, are, for example, organic peroxides, such as dibenzoylperoxide, tert.-butylperoctoate and azo compounds such as azodiisobutyric acid dinitrile. Redox systems, customary for use in dental materials, such as dibenzoylperoxide/dimethyl-p-toluidine and dibenzoylperoxide/trimethylbarbituric acid, may also be used.

The attached table reports values for bending strength, Rockwell-B-hardness and gloss which is a function of the capability of being polished of (i) the prosthetic appliances of the present invention and (ii) prior commercial hardened materials. The reported values establish that the prosthetic appliances of the present invention are superior to the prior art materials and have good mechanical characteristics and can be polished to a high gloss or sheen.

Test samples used to make measurements were made from a mixture of 10 g Bis-GMA, 0.1 g tert.-butylperoctoate and 20 g. amorphous silicic acid (which was silanated as disclosed in the following example) and hardened for 15 minutes at 105° C.

Bending resistance was determined in accordance with test specification ISO, draft for artificial dental filling materials (Document No. ISO/TC 106/WG 1/109, April 1973); Rockwell-B-hardness was determined in accordance with specification German Pat. No. DIN 50,103.

To test for capability of being polished, test samples having a diameter of 2cm and a thickness of 2mm were roughed over half their surface with sandpaper. The rough surface was smoothed with a buffing disc and then was polished with a customary polishing buff. The resulting sheen or gloss was first judged by visual comparison by an observer and then by means of a method used in the paper industry to determine the surface gloss of paper, cardboard or carton material. This objective method measures reflection under an angle of 45° with a Goniophotometer.

TEST PRINCIPLE TO DETERMINE SHEEN OR GLOSS:

Measurement is made, under all conditions, with an angle of incidence of illumination of 45°. The difference between maximum density or brightness of illumination of the sample at the peak of gloss (arbitrarily A), and the density of brightness of the sample by observation under an angle of 0° (arbitrarily B) is obtained. The density or brightness of illumination of a standard white sample made of barium sulphate, which observed under 45°, is obtained (arbitrarily C). The ratio of the difference (A-B) to the standard observation (C), i.e., (A-B)/C, has a value of ONE (or unity) added thereto. The result is the "gloss number" [(A-B)/C]+1. In practice it is only necessary to observe the maximum density or brightness of illumination (A) of the sample at the peak of gloss and to observe the density or brightness of illumination of the white standard under 45° (C) to determine the gloss number. The log, to base 10, of the gloss number is the "gloss value."

It is a requirement of dental prosthetic appliances, such as artificial teeth, crowns, bridges, caps, and jacket crowns, that they can be polished to a high gloss or sheen.

While it was to be expected that the described material has a better capability of being polished than known dental materials since the capability of being polished and to become glossy increases as the size of the filler particles decreases, it is surprising and it was not expected that this material which can be polished to a high gloss will still have the high abrasion resistance required for the dental prosthetic appliances. Investigation has shown that dental material made of commercial, artificial material without fillers is abraded at a rate about three times as much as are samples made in accordance with the present invention. Measurements were done by means of the apparatus described in the journal, Zahnarztliche Praxis,* Vol. VII/20 (1966), pp. 237 et seq. The capability of being polished is improved in the dental prosthetic appliances in accordance with the present invention, as shown by the experiments and entirely surprising, the abrasion resistance is also substantially improved. As noted hereinbefore, the latter was not to be expected since the art teaches that the capability of being polished to a high gloss and abrasion resistance are mutually opposed characteristics in dental materials.

*(Dental Practice)

The dental material in accordance with the present invention can be used as a filling for teeth and also as a material to make crowns, bridges, precase or preformed jacket crowns and caps, as well as artificial teeth. If crowns, bridges, or artificial teeth are made, at least the outer layer of the entire dental appliance should have the material including the filler. Thus, the outer layer or jacket 2 (FIG. 2) may differ from the material of core 1 which may be of a different material or may not include the filler. Commercial dental materials to make crowns and bridges have previously been proposed which contain a filler material of a few percent. The dental material in accordance with the present invention and the crowns, bridges, jackets and the like made therefrom have 50-70 percent (by weight) of the filler material. This high filler content is particularly advantageous in providing the dental appliance with the desired hardness and resistance against stress and strain when chewing.

EXAMPLE FOR THE MANUFACTURE OF A CROWN OR A BRIDGE IN ACCORDANCE WITH THE PRESENT INVENTION a. Silanating amorphous silicic acid 1.5kg of amorphous silicic acid, with an average particle diameter of 0.04 micrometers is added to 12 liters acetone at room temperature, while stirring. Thereafter, 30 g water are added. Sequentially, the following is added to this mixture:

First, 1.5 g dicyclohexylamine and 150 g trimethoxy(3-methacryloyloxy-propyl)-silane. After stirring for two hours and distilling off the acetone at 70° C under 20 mm pressure, a loose powder is obtained which is tempered for 20 hours at 100° C.

b. Mixing of single components and hardening of the dental material 0.1 g tert.-butylperoctoate is dissolved in 10 g bis-GMA. The solution is well mixed (kneaded) with 20 g of said silanated amorphous silicic acid.

The resulting paste-like mixture is hardened into a suitable bridge or crown shape in a mold form at 105° C in 15 minutes.

In the above example, the dental material containing as catalyst tert.-butylperoctoate in accordance with the present invention is polymerized by heat, i.e., the material is hardened by thermal polymerization. This method can be used when crowns, bridges or jackets are made.

The dental material can also be polymerized at room temperature; for example, when filling tooth cavities. A catalyst suitable for this process of polymerization is then used, such as, for example, dibenzoylperoxide/trimethylbarbituric acid or dibenzoylperoxide/dimethyl-p-toluidine.

Other illustrative organic binders include acrylic acid esters, especially bis-[4-(2-hydroxy-3-acryloyloxypropoxy)-phenyl]-dimethylmethane, ethyleneglycoldiacrylate and trimethylolpropanetriacrylate.

In the Example, the particles having an average particle size of 0.04 micrometer, the particles had a maximum particle size of less than 0.07 micrometer and at least half of the particles were in the range of 0.03 – 0.05 micrometer.

The particle size range of the additional fine glass is of 0.7 – 30 micrometer, preferably the particles have a particle size of not more than 5 micrometer.

Figure 2:
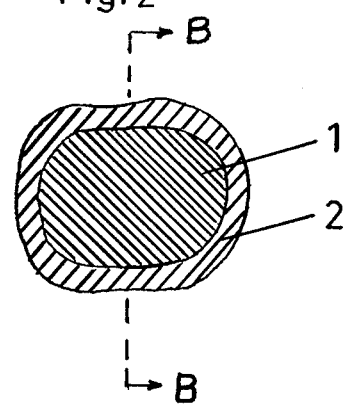
FIG. 2 is a cross-sectional view along the plane A—A of FIG. 2.

The outer jacket or sheath 2 of FIGS. 1 and 2 usually has a minimum thickness of 0.05 millimeter. The cap of FIG. 3 has a thickness in the range of 0.1 – 1 millimeter.

The diluting monomers are used to reduce the viscosity of the unhardened polymerizable binder and thereby to reduce the viscosity of the hardenable material too.

TABLE

| Binder | Filler | Bending Strength kg/mm$^2$ | Rockwell-B-Hardness | Gloss Visually Observed | Gloss Measured |
|---|---|---|---|---|---|
| Bis-GMA | Amorphous Silicic Acid* | 14.0 | 120 | High Gloss | 2.135 |
| Bis-GMA | Filler of Commercial Grade HL-72 | 11.5 | 117 | No High Gloss | 0.423 |

*mean particle size 0.04 micrometer

What is claimed:

1. Prosthetic dental appliance comprising a shaped body portion having at least one outer surface portion having an outer surface which is adapted to be polished and which is highly resistant to abrasion, at least said outer surface portion adjacent to said outer surface comprising a hardened binder resin selected from the group consisting of methacrylate resins and acrylic acid ester resins containing between about 30% and 80% by weight of said outer surface portion of amorphous silicic acid filler particles of a maximum particle size of about 0.07 micrometer, said amorphous silicic acid being selected from the group consisting of precipitated silicic acid, and silicic acid produced by flame hydrolysis.

2. The appliance of claim 1 wherein said hardened resin is a hardened methacrylate resin.

3. The appliance of claim 2 wherein said methacrylate resin is formed by the catalytic polymerization of at least one monomer selected from the group consisting of bis-[4-(2-hydroxy-3-methacryloyloxypropoxy)-phenyl]-dimethylmethane; and 2,2-bis-[p-(2-hydroxyethoxy)-phenyl]-propane-dimethacrylate; which may optionally also include admixed therewith triethyleneglycoldimethacrylate.

4. The appliance of claim 3 wherein at least half of the filler particles are of a size between about 0.03 and 0.05 micrometer.

5. The appliance of claim 4 wherein said filler particles comprise between about 50% and 70% of said outer surface portion.

6. The appliance of claim 1 wherein at least half of the filler particles are of a size between about 0.03 and 0.05 micrometer.

7. The appliance of claim 1 wherein said filler particles comprise between about 50% and 70% of said outer surface portion.

8. The appliance of claim 6 wherein said hardened polymeric matrix contains filler particles which have been treated with an organic silane to improve adhesion of said filler particles to said polymeric matric.

9. The appliance of claim 8 wherein said organic silane is trimethoxy-(3-methacryloyloxy-propyl)-silane.

10. The appliance of claim 5 wherein said hardened polymeric matrix contains filler particles which have been treated with an organic silane to improve adhesion of said filler particles to said polymeric matrix 11. The appliance of claim 10 wherein said organic silane is trimethoxy-(3-methacryloyloxy-propyl)-silane.

12. The appliance of claim 1 wherein said hardened polymeric matrix also contains small glass filler particles in an amount up to 25% by weight of the total filler particles.

13. The appliance of claim 1 wherein said shaped body contains a core and wherein said outer surface portion comprises a hardened shell surrounding at least a portion of said core.

14. The appliance of claim 13 which is a prosthetic tooth.

15. The appliance of claim 1 which is a prosthetic dental cap.

16. A hardenable material which when hardened is useful as a dental filling material and for the preparation of other prosthetic dental appliances comprising a polymerizable matrix selected from the group consisting of methylacrylates and acrylic acid esters having dispersed therein amorphous silicic acid particles of a maximum particle size of about 0.07 micrometer in an amount between about 30% and 80% by weight of said material, said amorphous silicic acid being selected from the group consisting of precipitated silicic acid, and silicic acid produced by flame hydrolysis.

17. The material of claim 16 wherein at least half of said amorphous silicic acid particles are of a particle size between about 0.03 and 0.05 micrometer.

18. The material of claim 17 wherein said filler particles comprise between about 50% and 70% of said material.

19. The material of claim 19 wherein said polymerizable matrix is a polymerizable methacrylate.

20. The material of claim 19 wherein said polymerizable material is at least one monomer selected from the group consisting of bis-[4-(2-hydroxy-3-methacryloyloxypropoxy)-phenyl]-dimethylmethane; and 2,2-bis-[p-(2-hydroxyethoxy)-phenyl]-propane-dimethacrylate.

21. The material of claim 20 wherein said material contains filler particles treated with an organic silane to improve adhesion of said filler particles to said polymeric matrix.

22. The material of claim 21 wherein said organic silane is trimethoxy-(3-methacryloyloxy-propyl)-silane.

23. The material of claim 21 which also contains a catalyst which will cause polymerization when the material is heated.

24. The material of claim 23 wherein said polymerizable organic matrix also contains dispersed therein small glass filler particles in an amount up to about 25% by weight of the total filler particles.

25. The material of claim 24 wherein said polymerizable matrix contains triethyleneglycoldimethacrylate.

26. The material of claim 20 wherein said polymerizable matrix contains triethylenglycoldimethacrylate.

27. The material of claim 16 wherein said amorphous silicic acid is silicic acid produced by flame hydrolysis.

28. The material of claim 16 wherein said amorphous silicic acid is precipitated silicic acid.

29. The material of claim 1 wherein said amorphous silicic acid is silicic acid produced by flame hydrolysis.

30. The material of claim 1 wherein said amorphous silicic acid is precipitated silicic acid.

* * * * *

UNITED STATES PATENT AND TRADEMARK OFFICE
CERTIFICATE OF CORRECTION

PATENT NO. : 4,029,632
DATED : June 14, 1977
INVENTOR(S) : Albert GROSS and Roland SCHAEFER It is certified that error appears in the above-identified patent and that said Letters Patent are hereby corrected as shown below:

Column 7, line 11, replace "claim 19" with --claim 18--.

Column 7, lines 11 and 12, correct the spelling of "polymerizable".

Signed and Sealed this

Twentieth Day of September 1977

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,029,632
DATED : June 14, 1977
INVENTOR(S) : Albert GROSS and Roland SCHAEFER It is certified that error appears in the above-identified patent and that said Letters Patent are hereby corrected as shown below:

Column 6, line 65, replace "methylacrylates" with -- methacrylates --.

Signed and Sealed this

Twenty-second Day of August 1978

[SEAL]

Attest:

RUTH C. MASON
Attesting Officer

DONALD W. BANNER
Commissioner of Patents and Trademarks